United States Patent [19]

Miller

[11] Patent Number: 5,071,748
[45] Date of Patent: Dec. 10, 1991

[54] MIXED BACULOVIRUS COMPOSITIONS AND USES THEREOF

[75] Inventor: David W. Miller, Belmont, Mass.

[73] Assignee: Genetics Institute, Inc., Cambridge, Mass.

[21] Appl. No.: 353,181

[22] Filed: May 15, 1989

Related U.S. Application Data

[63] Continuation of Ser. No. 905,729, Sep. 9, 1986, abandoned.

[51] Int. Cl.$^5$ .................. C12N 15/86; C12P 21/00
[52] U.S. Cl. ........................ 435/69.1; 435/320.1; 435/235.1; 935/32; 935/34; 935/57; 935/60; 935/64
[58] Field of Search .............. 435/69.1, 320.1, 235; 935/32, 34, 57, 60, 64

[56] References Cited

FOREIGN PATENT DOCUMENTS

| | | |
|---|---|---|
| 43943/85 | 1/1985 | Australia . |
| 0127839 | 12/1984 | European Pat. Off. . |
| 155476 | 9/1985 | European Pat. Off. . |
| 0222412 | 5/1987 | European Pat. Off. . |

OTHER PUBLICATIONS

Smith et al., *Molecular and Cellular Biology*, 3:2156-2165, 1983.
Smith et al., *Proc. Natl. Acad. Sci.*, (U.S.A.), 82:8404-8406, 1985 (Dec.).
*Mechanics of Patent Claim Drafting*, John L. Landis, Practicing Law Institute, N.Y., 2nd edition, pp. 202-203.
Miller et al., 1983, *Science* 219:715-721.
Adang & Miller, 1982, *J. Virol.*, 44(3):782-793.
Miller et al., 1983, *Virology* 126:376-380.
Lee et al., 1978, *J. Virol.* 27(3):754-767.
Miller, 1981, *J. Virol.* 39:973-976.
Smith et al., 1983, *Mol. Cell. Biol.* 3(12):2156-2165.
van Iddekinge, 1983, *Virology* 131:561-565.
Potter et al., 1980, *J. Invert. Path.* 36:431-432.
Pennock et al., 1984, *Mol. Cell. Biol.* 4(3):399-406.
Miller et al., 1982, *Genetic Engineering in Eucaryotes*, pp. 89-97 (Plenum Press, Luoquin et al. eds.).
Carter et al., 1984, "Viruses as Pest-Control Agents", *Biotech and Genetic Eng. Reviews*, vol. 1, pp. 375-405.
Iatrou et al., 1985, *J. Virol.* 54:436-445.
Maeda et al., 1985, *Nature*, 315:592.
Rohrmann et al., 1981, *J. Molec. Evolution* 17:329-333.
Miller, 1981, "A Virus Vector for Genetic Engineering in Invertebrates" in *Genetic Engineering in the Plant Sciences* (Panopoulos, ed.).
Smith et al., 1983, *J. Virol.* 46:584-593.
Miller et al., 1980, *J. Invert. Pathology*, 36:159-165.
Jewell et al., 1980, *J. Gen. Virol.* 48:161-175.
Miller et al., 1978, *App. Env. Microbiol.* 35(6):12061210.
Podgwaite, 1985, "Strategies for Field Use of Baculviruses" in *Viral Insecticides for Biological Control*, pp. 775-791 (Academic Press).
Miyamoto et al., 1985, *Mol. Cell. Biol.* 5(10):2860-2865.
Smith et al., 1983, *J. Virol.* 45(1):215-225.
Miller, Apr. 1987, *J. Cell. Biochem*, p. 172, abstr. No. MO17.
Miller et al., 1986, "An Insect Baculovirus Host-Vector System for High Level Expression of Foreign Genes" in *Genetic Engineering*, vol. 8 (Plenum Publishing Corp).

*Primary Examiner*—Richard A. Schwartz
*Assistant Examiner*—S. L. Nolan
*Attorney, Agent, or Firm*—Luann Cserr; Bruce Eisen

[57] ABSTRACT

A mixed composition polyhedral inclusion body (PIB) is provided which contains a mixture of nucleocapsids of at least two genetically distinct baculoviruses. At least one of the baculoviruses is genetically engineered to contain at least one heterologous gene. Followed ingestion of the mixed composition PIB by an insect host, a mixed viral infection ensues in the insect permitting the production therein of additional copies of the mixed composition PIB and the production of a heterologous protein encoded by the heterologous gene present in at least one of the baculoviruses.

17 Claims, No Drawings

MIXED BACULOVIRUS COMPOSITIONS AND USES THEREOF

This application is a continuation of application Ser. No. 905,729, filed Sept. 9, 1986, now abandoned.

BACKGROUND OF THE INVENTION

This invention relates to an improved method for producing heterologous proteins in insect cells, specifically in whole insect hosts.

Recent advances in the genetic engineering of baculoviruses have made possible the production of heterologous proteins in insect host cells grown in in vitro culture. One strategy which has achieved a certain measure of success involves (1) preparing a recombinant baculovirus which contains a DNA sequence encoding the heterologous protein operatively linked to the baculovirus polyhedrin promoter; (2) infecting cultured insect host cells with the recombinant virus; (3) growing the infected insect cells under suitable conditions for viral replication and protein expression and (4) recovering the desired heterologous protein thereby expressed from the insect cells or culture medium. Relatively high levels of expression of the desired protein can be obtained by the aforementioned strategy, in part because the polyhedrin promoter is such a strong promoter.

In considering the biology of this approach it should be kept in mind that baculoviruses are typically packaged in two forms: nucleocapsids may be occluded in the nucleus of infected cells in particles known as "polyhedral inclusion bodies" (PIBs) of which the predominant structural protein is polyhedrin or they may bud through the membrane of the infected cell thereby acquiring a membrane envelope to form non-occluded virus (NOV) particles. As a result of the usual deletion of all or part of the polyhedrin structural gene, or insertion of the heterologous gene within the polyhedrin gene locus involved in using the virus as an expression vector, the recombinant baculovirus used in the aforementioned approach is no longer capable of directing the synthesis of functional polyhedrin in infected cells. Horizontal transmission of the viral infection at the organismal level, i.e. from insect to insect, does not generally occur in the absence of the PIB form of the virus which cannot be produced without its principal structural protein, polyhedrin. Thus, infection with the recombinant virus results in the production of non-occluded viral progeny (NOVs) capable of spreading the infection from cell to cell within an infected insect or cell culture, but not from insect to insect.

Therefore, while the above-described recombinant baculovirus may be used to produce a heterologous protein in cultured insect cells or in a suitably inoculated individual insect host, production of the protein in whole insects in commercially significant amounts and/or horizontal transmission of the recombinant baculovirus would require the inoculation of a huge number of individual insects. Such extraordinary requirements of manpower, time and expense render such methods impracticable.

A new mixed viral system has now been discovered which permits for the first time the practical production of biologically and/or commercially significant amounts of a heterologous protein in whole insects and horizontal transmission of recombinant baculoviruses using a recombinant baculovirus which is itself defective with respect to polyhedrin production.

DETAILED DESCRIPTION OF THE INVENTION

The present invention provides a polyhedral inclusion body (PIB) containing a mixture of nucleocapsids of at least two genetically distinct baculoviruses. This mixed composition PIB (mPIB) contains nucleocapsids of at least one "recombinant" baculovirus which is incapable of directing the production of polyhedrin in infected insect cells (phenotypically, "PIB$^{31}$"), and nucleocapsids of at least one baculovirus which may be a wild-type, mutant or genetically modified virus, but must in any case, be capable of directing the production of polyhedrin in infected cells (phenotypically, "PIB+"). A "recombinant" baculovirus as the term is used herein means a baculovirus which lacks a functional polyhedrin gene and which contains at least one heterologous gene ("insert"), i.e. a gene not normally present in the baculovirus; or if normally present, present at a different locus in the wild-type baculovirus genome or under the transcriptional control of a different promoter or both, relative to the recombinant baculovirus. The biology and life cycle of numerous nuclear polyhedrosis viruses and corresponding insect and host cells are known in the art. Furthermore, a variety of transplacement vectors and methods of using such vectors to produce recombinant baculoviruses are now known in the art. See e.g. Pennock et al. and Miller et al., infra.

This invention encompasses mPIBs containing a recombinant nucleocapsid which contains more than one heterologous gene and thus is capable of directing the expression of more than one heterologous protein in infected insect cells. The invention further encompasses mPIBs containing three or more genetically distinct nucleocapsids In such embodiments the mPIB may contain three or more different recombinant nucleocapsids, e.g. where each different recombinant virus is capable of directing the expression of one or more different proteins Furthermore, an mPIB may contain nucleocapsids of two or more different baculoviral species.

Ingestion by an insect host of the mPIBs containing nucleocapsids of a PIB−, insert+baculovirus and nucleocapsids of a PIB+baculovirus in accordance with this invention results in a mixed viral infection in the insect such that both baculoviruses replicate in the infected cells. During the course of replication (a) the recombinant (PIB−, insert+) baculovirus and progeny thereof direct the expression of the heterologous gene (the "insert"), producing the protein encoded thereby; and (b) the PIB+baculovirus produces polyhedrin. This results in a high frequency of the progeny nucleocapsids being occluded in PIBs, thereby producing additional copies of the mPIB. The heterologous protein so produced may then be recovered from the insect and if desired may be further purified. Any heterologous protein for which a corresponding nucleotide sequence can be obtained may thus be produced in whole insects. Such proteins include therapeutic proteins useful in medical or veterinary applications, functional enzymes, and proteins which are toxic to at least one insect species. In the latter case, compositions containing the mPIB may be used as biological insecticides against the insect or insects which are suitable hosts for the virus and to which the heterologous protein is toxic.

In one aspect of the invention, the mPIB contains a mixture of nucleocapsids of two genetically distinct baculoviruses, as follows. The first baculovirus contains a gene encoding polyhedrin operatively linked to an expression control sequence permitting the baculovirus to direct the production of polyhedrin in the infected cell. Thus, the first baculovirus may be characterized phenotypically as PIB+. The PIB+baculovirus may be a wild-type strain of a nuclear polyhedrosis virus (NPV), e.g. AcNPV, BmNPV, RoNPV, OpNPV, DwNPV, TnNPV, etc. or may be a deletion or insertion variant, so long as it is capable of replicating (i.e. contains the "cis" genetic functions required for replication), being packaged in the mPIB and directing the production of functional polyhedrin in infected insect cells. The second baculovirus lacks a functional polyhedrin gene, e.g. because of an alteration such as a deletion or insertion within the polyhedrin gene locus. The second baculovirus does however contain the previously mentioned heterologous gene operatively linked to an expression control sequence permitting the baculovirus to direct the production in an infected insect cell of the heterologous protein encoded by the heterologous gene. The second baculovirus is characterized as $PIB^{31}$, insert+.

In one presently preferred embodiment the heterologous gene is inserted into the polyhedrin gene region of the second baculovirus such that the heterologous gene is under the transcriptional control of the polyhedrin promoter. Alternatively, the heterologous gene may be inserted into the baculovirus genome within the polyhedrin gene region, but operatively linked to a promoter other than the polyhedrin promoter, e.g. to the RSV-LTR, TED-LTR or to a baculovirus promoter other than the polyhedrin promoter, so long as the promoter is functional in infected insect cells. Similarly, the heterologous gene may be inserted at a site other than the polyhedrin gene locus, so long as the resultant recombinant baculovirus is capable of replicating, expressing the heterologous gene and being packaged in the mPIB, but incapable alone of forming PIBs.

mPIBs of this invention have been produced by simultaneously contacting NOVs of each of the baculoviruses to be packaged in the mPIBs (i.e. a PIB+virus and a PIB−, insert+virus) with insect host cells growing in vitro. Alternatively, the contacting may be effected by injecting the input viruses into whole insects. The contacting should be under conditions permitting baculoviral infection of the host or host cells. The viruses used for the co-infection are hereinafter referred to generally as the "input" viruses. The insect host cells are cultured using conventional methods known in the art, e.g. in suspension culture in spinner flasks or fermentation vessels or attached to the container surface in tissue culture flasks or dishes. The various procedures employed to culture the insects and insect cells, infect with baculoviruses, permit viral replication, screen and harvest the viral progeny are procedures known in the art, e.g. essentially as described in Miller et al., Genetic Enqineering, Vol. 8, pages 277-298, J. K. Setlow and A. Hollaender, eds. (Plenum Press, 1986). The total amount of virus added and the ratio of PIB+(e.g. wild type) to PIB−, insert+(altered) virus used in this initial infection can vary depending on the desired composition of the product mPIBs. Typically, the ratio is from about 1:1 to about 10:1, altered:wild type.

Numerous baculoviral strains and variants and corresponding permissive insect hosts have been identified. A variety of such strains are publicly available, e.g. the L-1 variant of *Autographa californica* NPV and the Bm-5 strain of *Bombyx mori* NPV, and may be used as the PIB+virus in the mPIBs of this invention. The insert+PIB−baculovirus may be obtained using any of several transplacement vectors and methods known in the art, see e.g. European published application No. 0 155 416; G. D. Pennock et al., 1984 *Mol. Cell. Biol.* 4(3):399–406; S. Maeda et al, 1985, *Nature* 315:592–594. One such transplacement vector, pIVEV, useful for inserting a passenger cDNA into the polyhedrin locus of the genome of the baculovirus *Autographa californica* has been deposited with the American Type Culture Collection and is available under accession number ATCC No. 39991.

In an exemplary experiment, *Spodoptera frugiperda* (Sf) cells growing in suspension culture in a spinner flask were inoculated with both wild type and recombinant input baculoviruses. The wild type virus was the L-1 variant of the nuclear polyhedrosis virus *A. californica*. The recombinant virus was a genotypically engineered AcNPV L-1 variant which contains in place of a functional polyhedrin gene, a cDNA encoding human tissue-type plasminogen activator (tPA). The recombinant baculovirus has been designated 3h8, and has been deposited with the American Type Culture Collection (ATCC) as ATCC No. VR2096. This virus may be characterized phenotypically as PIB−, t-PA+. The coinfection of the Sf cells was conducted at wild-type:- recombinant ratios of 1:1 and 1:10, i.e. at a multiplicity of infection of 1 or 10 for either virus, depending on the ratio of the two types.

This infection led to the production of NOVs of each type of input virus. It also led to the production of mPIBs which contain nucleocapsids of both input viruses. These results were demonstrated as follows. To analyze the type of NOV present, the cell supernatant containing the progeny NOVs was plaqued onto a monolayer of Sf cells and the phenotype of the resulting plaques scored. Plaques that contain PIBs were produced by wild type virus and those that lack PIBs by the recombinant tPA-containing virus. To determine the composition of the mPIBs, the mPIBs were first isolated from other material present in the cell culture. This was effected by centrifugation of the spinner flask contents to separate the large material, such as PIBs, from the smaller material, such as NOVs. The PIB-containing pellet was then washed several times with an SDS-containing solution to lyse and remove cellular debris contaminating the PIB pellet. The PIBs withstand this treatment and are isolated substantially free from cellular debris. The PIBs are suitable for the production of viral DNA, as follows. The PIB pellet is resuspended in sodium carbonate. This treatment causes the PIB to dissolve, releasing the embedded virus nucleocapsids into the solution. The nucleocapsids are recovered and concentrated by ultracentrifugation. The capsid pellet was resuspended in an SDS, tris, and EDTA solution, and proteinase K was added. The solution was incubated at 37° C. This treatment freed the viral DNA from the capsids. The DNA was further purified by conventional phenol extraction and ethanol precipitation.

Genotypic analysis of the purified DNA was effected by first subjecting the purified DNA to conventional restriction endonuclease (REN) digestion. The REN-digested DNA was electrophoretically separated on an agarose gel, and the separated DNA was transferred to a membrane filter according to the method of Southern (Maniatis et al., *Molecular Cloning—A Laboratory Manual,* Cold Spring Harbor Laboratory, 1982). It is at present most convenient to blot the gel bi-directionally. In this manner, the two filter replicas of the gel can be probed with one or the other of sequences diagnostic for either of the viral genomes. This method reveals the genotypic nature of the virus particles contained within the mPIBs, i.e., the presence or absence of a polyhedrin gene and the exogeneous DNA insert.

Thus, by the methods described above baculoviral mPIBs may be produced which are capable upon ingestion by a suitable insect host of producing a mixed viral infection in the host resulting in the production of progeny NOVs, progeny mPIBs and a heterologous protein in the infected insect. Baculoviral mPIBs are preferably designed and produced by the above-described methods such that the desired insect host is capable of being infected by the particular baculoviruses used and of supporting viral replication thereof As previously mentioned numerous baculoviruses and corresponding permissive host insects are known in the art.

While mPIBs may be used for large scale production in whole insects of therapeutic proteins, immunogens for vaccines, enzymes and other useful proteins, this invention is especially well suited for the biological control of insect pests. As in other embodiments the bioinsecticidal mPIB contains PIB+ and PIB−, insert+ baculoviruses which are infectious in the target (host) insect. As mentioned previously, the PIB−, insert+ baculovirus of bioinsecticidal mPIBs contain DNA (the insert) encoding a protein which is toxic to the target insect. The toxin may be lethal, paralytic or otherwise deleterious to the target insect. Such toxins may be recovered and purified from plants or from natural parasites or predators of the target or related insects. Natural parasites and predators of insects include bacteria, viruses, fungi and other insects. Candidate toxins may be screened for toxicity in the target insect and then cloned by conventional methods. Exemplary toxins include the toxic proteins from many *Bacillus thuringiensis* strains. Also suitable are toxins isolated from *Hymenoptera,* scorpions and spiders. Additionally, the toxin may be an enzyme known to enhance susceptibility to infection or which is itself deleterious to the target insect, e.g., chitinase. In such cases the mPIB may contain a transcription unit for such toxin, alone or together with a transcription unit for a second toxin.

This invention further encompasses compositions containing bioinsecticidal mPIBs, as described above, in admixture with agriculturally acceptable excipients including vehicles, carriers, binders, UV blockers, adhesives, humectants, insect attractants, etc. as are known in the art. Such compositions may be applied dry or in the form of a suspension, emulsion or foam to typical feeding areas of the target insect, including to vegetation, fruit, seed, soil or aquatic locales These compositions may also include conventional insecticidal agents and/or may be applied in con]unction with conventional insecticidal agents.

One advantage of the mPIBs of this invention is their limited effective persistance upon serial passage through insect hosts. More specifically, in the course of the research resulting in this invention, the composition of mPIBs has been observed to change from generation to generation upon serial passage, with the ratio of PIB+ to PIB−, insert+ consistently increasing in subsequent progeny. Thus, where the PIB+ baculovirus is a wild type virus, successive generations of mPIBs contain less and less recombinant (PIB−, insert+) virus, until eventual reversion to only wild type PIB is complete. The number of generations until loss of the PIB−, insert+ genotype can be conveniently modified by adjusting the ratio of input NOVs used to coinfect cultured cells to produce the mPIBs and/or by adjusting the number of mPIBs fed to the whole insects. The greater the proportion of PIB−, insert+ input NOVs to PIB+ input NOVs and/or the higher the number of mPIBs fed to the insects, the longer may be the effective duration (in terms of successive generations) of the PIB−, insert+ genotype of the mPIBs. The gradual loss of recombinant phenotype is advantageous since it limits any potential risk resulting from accidental or deliberate release of mPIBs into the environment.

Another advantage of this invention is the potential for altering or circumventing the host range of a particular baculovirus. For example, a recombinant virus engineered to contain a heterologous gene may not be able to replicate in a particular host because of naturally occuring host range limitations. Consequently, the heterologous gene would not have an opportunity to be expressed. In bio-insecticidal embodiments where the heterologous gene encodes a toxin, a target insect would not be susceptible to such a virus even if the virus in general had improved characteristics. Such limitations on host range will on many occasions be due to a defect in the ability of the non-susceptible host to support a complete virus replication cycle. One solution to this problem is to make use through the mixed PIB methodology of a non-engineered baculovirus that can replicate in the desired host/target species: NOVs of the virus that is replication proficient in the host/target are used to infect a cell line in which they are also replication proficient. The cell line is simultaneously coinfected with the engineered virus by the method already described. It is contemplated that the competent virus will provide the functions required by the incompetent virus (through complementation), and consequently both viruses will replicate. The engineered virus will be packaged in PIBs formed by the wild type virus. This will allow the resulting mPIBs to be used as a means to deliver the genetically engineered virus to the host/target insect. In this situation the mPIBs would dissolve in the midgut of the insect and cells will simultaneously be infected with both viruses. Again the complementation phenomenom should allow replication of the engineered virus and expression of the heterologous gene in the host/target insect. Should there not exist a cell line in which the non-engineered virus can replicate, this procedure can be carried out in live insects. In that case, the insects would be injected with NOVs of the two virus types. The resulting PIBs will be of mixed composition.

The following examples are provided to further illustrate the invention and are not intended to, nor should they be construed to limit the scope of the invention as defined by the claims which follow thereafter.

EXAMPLES

Example 1:

Production and use of mPIB:3h8/L-1

(a) The two viruses used in preparing mPIB:3h8/L-1 were as follows:

PIB+ baculovirus: L-1 variant of AcNPV

The L-1 variant of *Autographa californica* nuclear polyhedrosis virus (AcNPV) produces typical NPV plaques of high refractility under the light microscope owing to the production of PIBs in infected cells. Other polyhedrin-producing variants of AcNPV or other NPVs may also be used.

PIB−, insert+baculovirus: 3h8

The recombinant NPV, 3h8, may be obtained from the American Type Culture Collection, Rockville, Md. under accession number ATCC No. VR2096. 3h8 is a recombinant variant of AcNPV in which the majority of the polyhedrin structural gene has been deleted and replaced with a cDNA encoding human tissue plasminogen activator (t-PA) under the transcriptional control of the AcNPV polyhedrin promoter. 3h8 cannot direct the production of polyhedrin or PIBs and consequently produces viral plaques that are not refractile.

(b) Restriction Endonuclease (REN) Analysis of Viral DNA

The L-1 variant and the recombinant, 3h8, may be distinguished by their distinct plaque morphologies and by their REN patterns as analyzed electrophoretically on agarose gels. A convenient method to make this latter distinction is to conduct a conventional Southern blot of the REN digested DNA. EcoRI is well suited for this analysis, and the approximately 7.5 kb AcNPV REN fragment referred to to as the EcoRI I fragment is an appropriate probe. The wild type L-1 variant is seen to contain the intact, single EcoRI I fragment. The recombinant virus, 3h8, yields two inserted fragments of 4.5kb and 3.5kb since the inserted t-PA gene contains more than one EcoRI site. A mixture of these two viruses, L-1 and 3h8, will yield all three bands upon analysis of the DNA fragments produced with EcoRI. The relative autoradiographic intensity of the three bands is indicative of the ratio of the recombinant virus to the wild type virus.

(c) Production and analysis of the mPIBs

To produce the mixed composition PIBs, a spinner flask of *Spodoptera frugiperda* cells is infected by conventional methods, but with both the wild type L-1 and the recombinant 3h8 virus NOVs and at relatively high multiplicities of infection. Both viruses establish an infection in any one cell. At the late stage of the infection cycle when polyhedrin is ordinarily produced, the recombinant 3h8 virus directs the expression of the foreign gene that it contains (t-PA) and the wild type directs the expression of polyhedrin protein and the production of PIBs. As the PIBs condense from the polyhedrin protein and occlude the wild type virus, they simultaneously occlude the recombinant 3h8 virus. The ratio of input wild type L-1 to recombinant 3h8 NOVs can be varied so as to affect the ratio of the two virus types in the progeny PIBs.

This process can be experimentally demonstrated, as follows At the end of the infection cycle the progeny NOVs, present in the supernatant of the spinner flask, are characterized by plaqueing them on new cells. The increase in titre obtained demonstrates that the virus is growing. The ratio of PIB+ to PIB− progeny virus in the plaque assay reflects the ratio of the input virus.

The composition of the progeny PIBs in the infected cells can be determined by analyzing the genome structure of the virus particles contained within the progeny PIBs. These PIBs are collected by centrifugation of the infected cells and subsequent purification of the PIBs contained within. The virus nucleocapsids contained within the PIBs are freed by alkali dissolution. The viral DNA is purified and digested with EcoRI, and the restriction fragments so produced are separated by agarose gel electrophoresis. Southern blotting of the gel and probing of the blot with the viral EcoRI I fragment by conventional methods revealed the presence of both viral genomes. The intensity of the bands reveals their relative abundance.

Example 2:

Horizontal Transmission of Mixed Viral Infection mPIB:3h8/L-1 was produced by the method of Example 1 at two different L-1:3h8 moi ratios, i.e., 1:1 and 1:10. At the end of the infection cycle the mPIBs were harvested, and the harvested mPIBs fed to *Heliothis virescens* caterpillars. Feeding was effected by spreading the mPIBs onto the surface of the artificial diet on which the caterpillars were raised. Typically $10^5$–$10^6$ mPIBs/caterpillar were placed on the food source. Within 5 days the caterpillars usually died from virus infection. The dead or nearly dead caterpillars were collected and homogenized in a cell culture medium, TC-100, adjusted to be 5mM in cysteine, (approximately 5 caterpillars/5ml medium). The homogenate was centrifuged at 10,000 xg to pellet the PIB-containing debris. The supernatant, which contains NOVs, was filtered through a 0.45 micron filter to remove microbial contamination and then plaqued onto fresh *Spodoptera frugiperda* cells. After approximately five days the plaques were developed sufficiently that their morphology (PIB+ vs PIB−, insert+) could be ascertained and the L-1:3h8 ratio determined.

To purify the PIBs, the 10,000 xg pellet was resuspended in 20 ml 0.1% SDS, homogenized, and filtered through two layers of cheesecloth. The filtrate was centrifuged at 6000×g for 10 minutes, and the pellet resuspended in 0.1% SDS. The centrifugation was repeated, and the pellet resuspended in water. This suspension was centrifuged again, and the pellet again resuspended in water to produce a PIB suspension. Analysis of the nucleocapsid contents of the PIBs so produced (by the methods described previously for mPIBs produced in cell culture) showed that these progeny PIBs contained both input nucleocapsids. The ratio of wild type to 3h8 virus, however, had increased relative to the original input ratio. Subsequent progeny mPIBs produced by serial passage through caterpillars were also found to contain both types of nucleocapsids, but again, with a gradually increasing ratio of wild type to 3h8 virus.

What is claimed is:

1. A mixed composition polyhedral inclusion body (PIB) which comprises:
   a) a first baculovirus which is capable of producing polyhedrin protein, and
   b) a second baculovirus which has been genetically engineered so that it is capable of producing a heterologous protein and is not capable of producing the polyhedrin protein, which mixed composition, when co-infected into a susceptible host, results in co-occlusion of the two different baculoviruses and expression of the heterologous protein.

2. A PIB of claim 1 wherein the first baculovirus is a wild-type nuclear polyhedrosis virus (NPV).

3. A PIB of claim 1, wherein the second baculovirus contains a heterologous gene inserted at the polyhedrin bene locus and operatively linked to an expression control sequence.

4. A PIB of claim 3, wherein the expression control sequences comprise the polyhedrin promoter.

5. A PIB of claim 1, wherein the second baculovirus contains a deletion of at least part of the polyhedrin gene.

6. A PIB of claim 1, wherein the heterologous gene encodes an enzyme or therapeutic protein.

7. A method for producing PIBs of claim 1 which comprises infecting a cell culture of baculovirus-permissive cells with the genetically distinct baculoviruses and culturing the infected cells under suitable conditions permitting viral replication and PIB production.

8. A method of claim 7 which further comprises recovering the PIBs so produced from the infected insect cell culture.

9. A method for producing PIBs of claim 1 which comprises injecting an insect with the genetically distinct baculoviruses under suitable conditions permitting viral replication and PIB production in cells of the infected insect.

10. A method of claim 9 which further comprises recovering the PIBs so produced from the infected insect 11. A method for coinfecting an insect host with a first baculovirus capable of directing the production of polyhedrin in infected cells and with a second baculovirus lacking a functional polyhedrin-encoding gene but containing a heterologous gene encoding a heterologus protein, the method comprising allowing the insect host to ingest an effective amount of PIBs of claim 1 permitting the production of a mixed viral infection in the insect host.

12. A method for producing a PIB useful in the production of a heterologous protein which comprises coinfecting an insect host by the method of claim 11 and growing the insect under suitable conditions and for an appropriate period of time permitting viral replication and PIB production.

13. A method of claim 12 which further comprises recovering PIBs so produced from the infected insect.

14. A method for producing a heterologous protein in an insect which comprises coinfecting the insect by the method of claim 11 and growing the insect under suitable conditions and for an effective period of time permitting viral replication and the production of the heterologous protein encoded for by the heterologous gene present in one of the baculoviruses.

15. A method of claim 14 which further comprises recovering the heterologous protein from the insect in which it is produced.

16. A method of claim 15 which further comprises purifying the heterologous proteins so recovered, 17. A method of claim 14, wherein the heterologous proteins is a therapeutic protein or enzyme.

* * * * *